United States Patent
Shimokawa et al.

(10) Patent No.: US 11,413,273 B2
(45) Date of Patent: Aug. 16, 2022

(54) PROPHYLACTIC OR THERAPEUTIC AGENT FOR PULMONARY HYPERTENSION COMPRISING UNSATURATED 5-MEMBERED HETEROCYCLE-CONTAINING COMPOUND

(71) Applicant: TOHOKU UNIVERSITY, Miyagi (JP)

(72) Inventors: Hiroaki Shimokawa, Miyagi (JP); Yoshiteru Oshima, Miyagi (JP); Haruhisa Kikuchi, Miyagi (JP); Jyunken Aoki, Miyagi (JP); Takayuki Doi, Miyagi (JP); Kuniyuki Kano, Miyagi (JP); Kimio Satoh, Miyagi (JP); Ryo Kurosawa, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 722 days.

(21) Appl. No.: 16/317,967

(22) PCT Filed: Jul. 14, 2017

(86) PCT No.: PCT/JP2017/025822
§ 371 (c)(1),
(2) Date: Apr. 23, 2019

(87) PCT Pub. No.: WO2018/012634
PCT Pub. Date: Jan. 18, 2018

(65) Prior Publication Data
US 2021/0299093 A1    Sep. 30, 2021

(30) Foreign Application Priority Data

Jul. 15, 2016 (JP) .............................. JP2016-140474

(51) Int. Cl.
*A61K 31/404* (2006.01)
*A61K 31/341* (2006.01)
*A61K 31/381* (2006.01)

(52) U.S. Cl.
CPC .......... *A61K 31/404* (2013.01); *A61K 31/341* (2013.01); *A61K 31/381* (2013.01)

(58) Field of Classification Search
None
See application file for complete search history.

(56) References Cited

FOREIGN PATENT DOCUMENTS

| JP | 9-59249 | 3/1997 |
| JP | 2010-173956 | 8/2010 |
| WO | 99/53758 | 10/1999 |

OTHER PUBLICATIONS

Kikuchi et al., "Revised Structure and Synthesis of Celastramycin A, A Potent Innate Immune Suppressor", 2009, Org. Lett., 11(8), pp. 1693-1695. (Year: 2009).*
Kurosawa et al., "Identification of Celastramycin as a Novel Therapeutic Agent for Pulmonary Arterial Hypertension High-Throughput Screening of 5562 Compounds", 2019, Circ. Res., 125(3), pp. 309-327. (DOI: 10.1161/CIRCRESAHA.119.315229) (Year: 2019).*
International Search Report dated Sep. 12, 2017 in corresponding International (PCT) Application No. PCT/JP2017/025822.
International Preliminary Report on Patentability dated Sep. 12, 2017 in corresponding International (PCT) Application No. PCT/JP2017/025822, with English translation.
Tomita et al., "ZFC3H1, a Zinc Finger Protein, Modulates IL-8 Transcription by Binding with Celastramycin A, a Potential Immune Suppressor", PLOS One, vol. 9, Issue 9, 2014, e108957, pp. 1-10.
Damas et al., "Soluble CD40 Ligand in Pulmonary Arterial Hypertension Possible Pathogenic Role of the Interaction Between Platelets and Endothelial Cells", Circulation, vol. 110, No. 8, 2004, pp. 999-1005.
Hong-Fang et al., "Effects of hydrogen sulfide on vascular Inflammation in pulmonary hypertension induced by high pulmonary blood flow, experiment with rats" National Medical Journal China, vol. 88, No. 32, 2008, pp. 2235-2239, with English abstract.
Kimura et al., "Alleviation of Monocrotaline-Induced Pulmonary Hypertension by Antibodies to Monocyte Chemotactic and Activating Factor/Monocyte Chemoattractant Protein-1", Laboratory Investigation, vol. 78, No. 5, 1998, pp. 571-581.

(Continued)

*Primary Examiner* — My-Chau T. Tran
(74) *Attorney, Agent, or Firm* — Wenderoth, Lind & Ponack, L.L.P.

(57) ABSTRACT

The present invention provides a preventive or therapeutic agent for pulmonary hypertension, including a compound represented by the following formula (I) or a salt thereof: where: —A— represents —NH—, —S—, or —O—; $R^1$ and $R^2$ are identical to or different from each other, and each represent a hydrogen atom or an alkyl group; $R^3$ represents a hydrogen atom, a halogen atom, or an alkyl group; $R^4$ represents a hydrogen atom or an alkyl group; $R^5$ represents a hydrogen atom or an alkyl group; $R^6$ and $R^7$ are identical to or different each other, and each represent a hydrogen atom, a halogen atom, or an alkyl group; and $R^6$ and $R^7$ may form an unsaturated hydrocarbon six-membered ring together with a carbon atom to which $R^6$ is bonded and a carbon atom to which $R^7$ is bonded.

12 Claims, 4 Drawing Sheets

(56) References Cited

OTHER PUBLICATIONS

Ikeda et al., "Anti-monocyte chemoattractant protein-1 gene therapy attenuates pulmonary hypertension in rats", Am J Physiol Heart Circ Physiol, vol. 283, No. 5, 2002, pp. H2021-2028.
Kennedy et al., "Amiodarone Causes Acute Oxidant Lung Injury in Ventilated and Perfused Rabbit Lungs", Journal of Cardiovascular Pharmacology, vol. 12, No. 1, 1988, pp. 23-36.
Kurosawa et al., "Abstract 14575: Celastramycin Inhibits Pulmonary Arterial Smooth Muscle Cell Proliferation and Ameliorates Hypoxia-induced Pulmonary Hypertension in Mice", Circulation, vol. 134, No. Suppl. 1, 2016, Abstract 14575, 5 pages
Rabinovitch et al., "Molecular pathogenesis of pulmonary arterial hypertension", The Journal of Clinical Investigation, vol. 122, No. 12, 2012, pp. 4306-4313.
Hosokawa et al., "Novel Selective Nfkb Inhibitor Compound Suppresses Pulmonary Arterial Smooth Muscle Cell Proliferation for Pulmonary Arterial Hypertension", American Thoracic Society International Conference Abstracts, B63, A3406, 2012, 1 page.

* cited by examiner

PROPHYLACTIC OR THERAPEUTIC AGENT FOR PULMONARY HYPERTENSION COMPRISING UNSATURATED 5-MEMBERED HETEROCYCLE-CONTAINING COMPOUND

TECHNIC FIELD

The present invention relates to a preventive or therapeutic agent for pulmonary hypertension.

BACKGROUND ART

Pulmonary hypertension is a disease involving increased blood pressure in pulmonary arteries, which carry blood from heart to lungs, leading to impaired cardiac and pulmonary functions, and is a disease quite different from a symptom generally called "hypertension", In addition, pulmonary hypertension is a severe disease with, high lethality, and hence there is an urgent need to develop a therapeutic method therefor.

Conventional treatments for pulmonary hypertension include vasodilation treatment using a catheter, and treatment such as surgical removal of thrombus, but less invasive therapeutic methods are desired. In addition, a vasodilator or the like is known as medication (e.g., Non-patent Literature 1), but there are still a large number of patients that cannot be saved by such therapeutic method. Thus, there is a strong demand for further development of a therapeutic agent for pulmonary hypertension.

CITATION LIST

Non-Patent Literature

NPL 1: J Clin Invest. 2012; 122(12); 4306-4313
NPL 2: PLOS ONE 2014; Vol 9, Issue 9, e108957: 1-10
NPL 3: American Thoracic Society International Conference Abstracts 2012, B63, A3406

SUMMARY OF INVENTION

Technical Problem

An object of the present invention is to provide a novel preventive or therapeutic agent for pulmonary hypertension containing as an active ingredient a compound that has not been known for a therapeutic effect on pulmonary hypertension heretofore.

Solution to Problem

Under such circumstances, the inventors of the present invention have investigated thousands of kinds of compounds. As a result, the inventors have found that a compound represented by the general formula (I) or a salt thereof to be described later suppresses excessive proliferation of pulmonary artery smooth muscle cells, which is supposed to be one of the causes for pulmonary hypertension, and has preventive and therapeutic effects on pulmonary hypertension. The present invention is based on such novel findings.

Thus, the present invention provides the following items:

Item 1. A preventive or therapeutic agent for pulmonary hypertension, including a compound represented by the following formula (I) or a salt thereof:

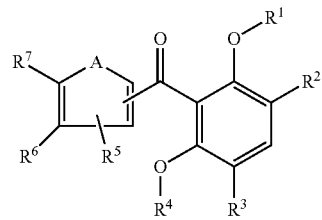

where: —A— represents —NH—, —S—, or —O—; $R^1$ and $R^2$ are identical to or different from each other, and each represent a hydrogen atom or an alkyl group; $R^3$ represents a hydrogen atom, a halogen atom, or an alkyl group; $R^4$ represents a hydrogen atom or an alkyl group; $R^5$ represents a hydrogen atom or an alkyl group; $R^6$ and $R^7$ are identical to or different from each other, and each represent a hydrogen atom, a halogen atom, or an alkyl group; and $R^6$ and $R^7$ may form an unsaturated hydrocarbon six-membered ring together with a carbon atom to which $R^6$ is bonded and a carbon atom to which $R^7$ is bonded.

Item 2. The preventive or therapeutic agent for pulmonary hypertension according to Item 1, wherein —— represents —NH—.

Item 3. The preventive or therapeutic agent for pulmonary hypertension according to Item 1 or 2, wherein $R^1$ and $R^4$ both represent hydrogen atoms.

Item 4. The preventive or therapeutic agent for pulmonary hypertension according to any one of Items 1 to 3, wherein $R^5$ represents a hydrogen atom.

Item 5. The preventive or therapeutic agent for pulmonary hypertension according to any one of Items 1 to 4, wherein $R^6$ and $R^7$ each represent a hydrogen atom or a halogen atom, and at least one thereof represents a halogen atom.

Item 6. The preventive therapeutic agent for pulmonary hypertension according to any one of Items 1 to 5, wherein $R^3$ represents a halogen atom or an alkyl group.

Item 7. The preventive or therapeutic agent for pulmonary hypertension according to any one of Items 1 to 6, wherein $R^2$ represents a hydrogen atom or an alkyl group.

Item 8. The preventive or therapeutic agent for pulmonary hypertension according to Item 1,
wherein —A— represents —NH—,
wherein $R^1$, $R^4$, and $R^5$ all represent hydrogen atoms,
wherein $R^2$ represents a hydrogen atom or an alkyl group,
wherein $R^3$ represents a halogen atom or an alkyl group, and
wherein $R^6$ and $R^7$ each represent a hydrogen atom or a halogen atom, and at least one thereof represents a halogen atom.

Item 9. The preventive or therapeutic agent for pulmonary hypertension according to any one of Items 1 to 8, wherein $R^2$ represents a linear alkyl group having 4 or more carbon atoms.

Item 10. The preventive or therapeutic agent for pulmonary hypertension according to any one of Items 1 to 8, wherein $R^2$ represents a linear alkyl group having 7 or more carbon atoms.

Item 11. The preventive or therapeutic agent for pulmonary hypertension according to any one of Items 1 to 10, wherein the preventive or therapeutic agent for pulmonary hypertension includes an orally administered agent.

Item 12-1. A method of preventing or treating pulmonary hypertension, including administering an effective dose of a compound represented by the following formula (I) or a salt thereof:

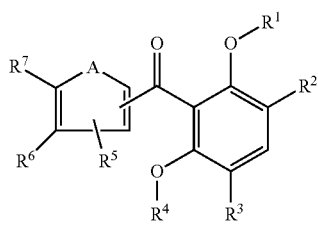 (I)

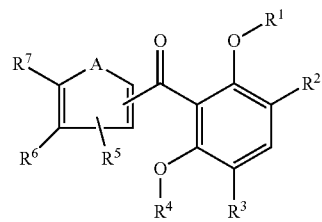 (I)

where: —A— represents —NH—, —S—, or —O—; $R^1$ and $R^2$ are identical to or different from each other, and each represent a hydrogen atom or an alkyl group; $R^3$ represents a hydrogen atom, a halogen atom, or an alkyl group; $R^4$ represents a hydrogen atom or an alkyl group; $R^5$ represents a hydrogen atom or an alkyl group; $R^6$ and $R^7$ are identical to or different from each other, and each represent a hydrogen atom, a halogen atom, or an alkyl group; and $R^6$ and $R^7$ may form an unsaturated hydrocarbon six-membered ring together with a carbon atom to which $R^6$ is bonded and a carbon atom to which $R^7$ is bonded.

Item 12-2. The method according to Item 12-1, wherein —A— represents —NH—.

Item 12-3. The method according to Item 12-1 or 12-2, wherein $R^1$ and $R^4$ both represent hydrogen atoms.

Item 4. The method according to any one of Item 12-1 to 12-3, wherein $R^5$ represents a hydrogen atom.

Item 12-5. The method according to any one of Items 14-1 to 12-4, wherein $R^6$ and $R^7$ each represent a hydrogen atom or a halogen atom, and at least one thereof represents a halogen atom.

Item 12-6. The method according to any one of Items 12-1 to 12-5, wherein $R^3$ represents a halogen atom or an alkyl group.

Item 12-7. The method according to any one of Items 12-1 to 12-6, wherein $R^2$ represents a hydrogen atom or an alkyl group.

Item 12-8. The method according to Item 12-1, wherein —A— represents —NR—, wherein $R^1$, $R^4$, and $R^5$ all represent hydrogen atoms, wherein $R^2$ represents a hydrogen atom or an alkyl group, wherein $R^3$ represents a halogen atom or an alkyl group, and wherein $R^6$ and $R^7$ each represent a hydrogen atom or a halogen atom, and least one thereof represents a halogen atom.

Item 12-9. The method according any one of Items 12-1 to 12-8, wherein $R^2$ represents a linear alkyl group having 4 or more carbon atoms.

Item 12-10. The method according to any one of Items 12-1 to 12-8, wherein $R^2$ represents a linear alkyl group having 7 or more carbon atoms.

Item 12-11. The method according to any one of Items 12-1 to 12-10, wherein the administering includes orally administering the compound or the salt thereof.

Item 13-1. A use of a compound represented by the following formula (I) or a salt thereof, for manufacture of a preventive or therapeutic agent for pulmonary hypertension:

where: —A— represents —NH—, —S—, or —O—; $R^1$ and $R^2$ are identical to or different from each other, and each represent a hydrogen atom or an alkyl group; $R^3$ represents a hydrogen atom, a halogen atom, or an alkyl group; $R^4$ represents a hydrogen atom or an alkyl group; $R^5$ represents a hydrogen atom or an alkyl group; $R^6$ and $R^7$ are identical to or different from each other, and each represent a hydrogen atom, a halogen atom, or an alkyl group; and $R^6$ and $R^7$ may form an unsaturated hydrocarbon six-membered ring together with a carbon atom to which $R^6$ is bonded and a carbon atom to which $R^7$ is bonded.

Item 13-6. The use according to Item 13-1, wherein —A— represents —NH—.

Item 13-3. The use according to Item 13-1 or 13-2, wherein $R^1$ and $R^4$ both represent hydrogen atoms.

Item 13-4. The use according to any one of Items 13-1 to 13-3, wherein $R^5$ represents a hydrogen atom.

Item 13-5. The use according to any one of Items 13-1 to 13-4, wherein $R^6$ and $R^7$ each represent a hydrogen atom or a halogen atom, and at least one thereof represents a halogen atom.

Item 13-6. The use according to any one of Items 13-1 to 13-5, wherein $R^3$ represents a halogen atom or an alkyl group.

Item 13-7. The use according to any one of Items 13-1 to 13-6, wherein $R^2$ represents a hydrogen atom or an alkyl group.

Item 13-8. The use according to Item 13-1, wherein —A— represents —NH—, wherein $R^1$, $R^4$, and $R^5$ all represent hydrogen atoms, wherein $R^2$ represents a hydrogen atom or an alkyl group, wherein $R^3$ represents a halogen atom or an alkyl group, and wherein $R^6$ and $R^7$ each represent a hydrogen atom or a halogen atom, and at least one thereof represents a halogen atom.

Item 13-9. The use according to any one of Items 13-1 to 13-8, wherein $R^2$ represents a linear alkyl group having 4 or more carbon atoms.

Item 13-10. The use according to any one of Items 13-1 to 13-8, wherein $R^2$ represents a linear alkyl group having 7 or more carbon atoms.

Item 13-11. The use according to any one of Items 13-1 to 13-10, wherein the preventive or therapeutic agent for pulmonary hypertension includes an orally administered agent.

Item 14-1. A compound represented by the following formula (I) or a salt thereof, for use in prevention or treatment of pulmonary hypertension:

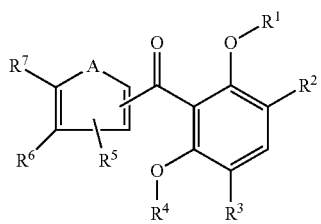

(I)

where: —A— represents —NH—, —S—, or —O—; $R^1$ and $R^2$ are identical to or different from each other, and each represent a hydrogen atom or an alkyl group; $R^3$ represents a hydrogen atom, a halogen atom, or an alkyl group; $R^4$ represents a hydrogen atom or an alkyl group; $R^5$ represents a hydrogen atom or an alkyl group; $R^6$ and $R^7$ are identical to or different from each other, and each represent a hydrogen atom, a halogen atom, or an alkyl group; and $R^6$ and $R^7$ may form an unsaturated hydrocarbon six-membered ring together with a carbon atom to which $R^6$ is bonded and a carbon atom to which $R^7$ is bonded.

Item 14-2. The compound or the salt thereof according to Item 14-1, wherein —A— represents —NH—.

Item 14-3. The compound or the salt thereof according to Item 14-1 or 14-2, wherein $R^1$ and $R^4$ both represent hydrogen atoms.

Item 14-4. The compound or the salt thereof according to any one of Items 14-1 to 14-3, wherein $R^5$ represents a hydrogen atom.

Item 14-5. The compound or the salt thereof according to any one of Items 14-1 to 14-4, wherein $R^6$ and $R^7$ each represent a hydrogen atom or a halogen atom, and at least one thereof represents a halogen atom.

Item 14-6. The compound or the salt thereof according to any one of Items 14-1 to 14-5, wherein $R^3$ represents a halogen atom or an alkyl group.

Item 14-7. The compound or the salt thereof according to any one of Items 14-1 to 14-6, wherein $R^2$ represents a hydrogen atom or an alkyl group.

Item 14-8. The compound or the salt thereof according to Item 14-1,
wherein —A— represents —NH—,
wherein $R^1$, $R^4$, and $R^5$ all represent hydrogen atoms,
wherein $R^2$ represents a hydrogen atom or an alkyl group,
wherein $R^3$ represents a halogen atom or an alkyl group, and
wherein $R^6$ and $R^7$ each represent a hydrogen atom or a halogen atom, and at least one thereof represents a halogen atom.

Item 14-9. The compound or the salt thereof according to any one of Items 14-1 to 14-8, wherein $R^2$ represents a linear alkyl group having 4 more carbon atoms.

Item 14-10. The compound or the salt thereof according to any one of Items 14-1 to 14-8, wherein $R^2$ represents a linear alkyl group having 7 or more carbon atoms.

Item 14-11. The compound or the salt thereof according to any one of Items 14-1 to 14-10, wherein the compound or the salt thereof is for use in prevention or treatment of pulmonary hypertension by oral administration.

Advantageous Effects of Invention

According to the present invention, the novel preventive or therapeutic agent for pulmonary hypertension can be provided by using the compound represented by the general formula (I) or the salt thereof.

DESCRIPTION OF EMBODIMENTS

Figure 1:
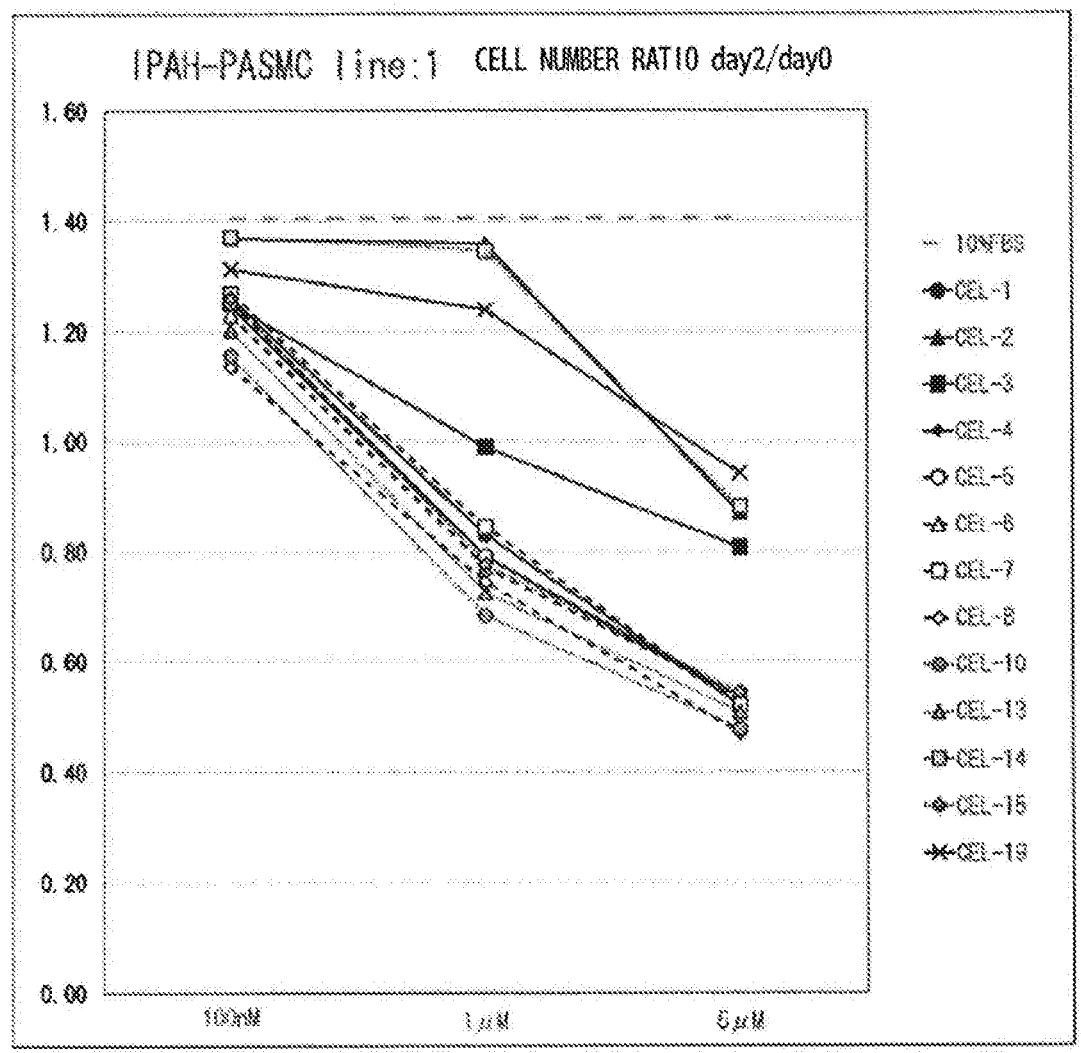
FIG. 1 is a graph for showing the influences of various compounds on the proliferation of pulmonary artery smooth muscle cells from patients with pulmonary hypertension measured in Example 1.

Preventive or Therapeutic Agent for Pulmonary Hypertension

The present invention provides a preventive or therapeutic agent for pulmonary hypertension containing a compound represented by the following formula (I) or a salt thereof:

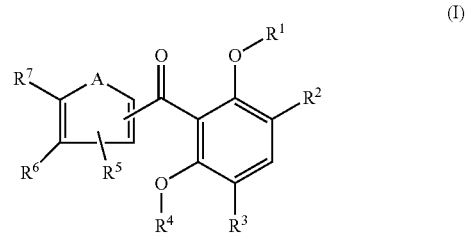

(I)

where: —A— represents —NH—, —S—, or —O—; $R^1$ and $R^2$ are identical to or different from each other, and each represent a hydrogen atom or an alkyl group; $R^3$ represents a hydrogen atom, a halogen atom, or an alkyl group; $R^4$ represents a hydrogen atom or an alkyl group; $R^5$ represents a hydrogen atom or an alkyl group; $R^6$ and $R^7$ are identical to or different from each other, and each represent a hydrogen atom, a halogen atom, or an alkyl group; and $R^6$ and $R^7$ may form an unsaturated hydrocarbon six-membered ring together with a carbon atom to which $R^6$ is bonded and a carbon atom to which $R^7$ is bonded. Herein, the compound represented by the formula (I) is sometimes referred to simply as compound (I).

In the present invention, the "alkyl group" refers to a linear or branched saturated hydrocarbon group, unless otherwise specified, and is, for example, a linear or branched saturated hydrocarbon group having 1 to 20 carbon atoms. Specific examples of the alkyl group include a methyl group, an ethyl group, a n-propyl group, an isopropyl group, a n-butyl group, an isobutyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, and a n-icosyl group.

In the present invention, examples of the "halogen atom" include fluorine, chlorine, bromine, and iodine atoms, unless otherwise specified.

In the general formula (I), —A— represents —NH—, —S—, or —O—. In the general formula (I), —A— preferably represents —NH—.

In the general formula (I), $R^1$ represents a hydrogen atom or an all group. In the general formula (I), $R^1$ preferably represents a hydrogen atom.

In the general formula (I), examples of the alkyl group represented by $R^1$ include those described above. Of those, a lower alkyl group is preferred. In the general formula (I), the alkyl group represented by $R^1$ is, for example, preferably an alkyl group having 1 to 6 carbon atoms, more preferably an alkyl group having 1 to 3 carbon atoms, still more preferably a methyl group.

In the present invention, the lower alkyl group is, for example, an alkyl group having 1 to 6 carbon atoms, preferably 1 to 3 carbon atoms out of the alkyl groups described above.

In the general formula (I), $R^2$ is identical to or different from $R^1$, and represents a hydrogen atom or an alkyl group. In the general formula (I), $R^2$ preferably represents an alkyl group.

In the general formula (I), examples of the alkyl group represented by $R^2$ include those described above. The alkyl group may be linear or branched, and is preferably linear. In addition, the alkyl group represented by $R^2$ is preferably an alkyl group having a relatively long chain from the viewpoint of suppressing the proliferation of pulmonary artery smooth muscle cells. The alkyl group represented by $R^2$ is, for example, an alkyl group having 1 or more carbon atoms, preferably an alkyl group having 3 or more carbon atoms, more preferably an alkyl group having 4 or more carbon atoms, more preferably an alkyl group having 5 or more carbon atoms, more preferably an alkyl group having 7 or more carbon atoms, more preferably an alkyl group having 9 or more carbon atoms, still more preferably an alkyl group having 11 or more carbon atoms. In addition, the upper limit of the number of carbon atoms is not particularly limited, but the alkyl group represented by $R^2$ is, for example, an alkyl group having 20 or less carbon atoms, preferably an alkyl group having 19 or less carbon atoms, more preferably an alkyl group having 17 or less carbon atoms, more preferably an alkyl group having 15 or less carbon atoms, still more preferably an alkyl group having 13 or less carbon atoms.

In the general formula (I), $R^3$ represents a hydrogen atom, a halogen atom, or an alkyl group. In the general formula (I), $R^3$ preferably represents, for example, a halogen atom or an alkyl group.

In the general formula (I), examples of the halogen atom represented by $R^3$ include fluorine, chlorine, bromine, and iodine atoms. Of those, for example, chlorine and bromine atoms are preferred.

In the general formula (I), examples of the alkyl group represented by $R^3$ include those described above. Of those, a lower alkyl group is preferred. In the general formula (I), the alkyl group represented by $R^3$ is, for example, preferably a linear or branched alkyl group having 1 to 6 atoms, more preferably a linear or branched alkyl group having 1 to 3 carbon atoms, particularly preferably a methyl group.

In the general formula (I), $R^4$ represents a hydrogen atom or an alkyl group. In the general formula (I), $R^4$ preferably represents a hydrogen atom.

In the general formula (I), examples of the alkyl group represented by $R^4$ include those described above. Of those, a lower alkyl group is preferred. In the general formula (I), the alkyl group represented by $R^4$ is, for example, preferably a linear or branched alkyl group having 1 to 6 carbon atoms, more preferably a linear or branched alkyl group having 1 to 3 carbon atoms, particularly preferably a methyl group.

In the general formula (I), $R^5$ represents a hydrogen atom or an alkyl group. In the general formula (I), $R^5$ preferably represents a hydrogen atom.

In the general formula (I), examples of the alkyl group represented by include those described above. Of those, a lower alkyl group is preferred. In the general formula (I), the alkyl group represented by $R^5$ is, for example, preferably a linear or branched alkyl group having 1 to 6 carbon atoms, more preferably a linear or branched alkyl group having 1 to 3 carbon atoms, particularly preferably a methyl group.

In the general formula (I), $R^6$ represents a hydrogen atom, a halogen atom, or an alkyl group. In the general formula (I), $R^6$ represents, for example, a hydrogen atom or a halogen atom. Of those, a halogen atom is preferred.

In the general Formula (I), examples of the halogen atom represented by $R^6$ include fluorine, chlorine, bromine, and iodine atoms. Of those, for example, chlorine and bromine atoms are preferred.

In the general formula (I), examples of the alkyl group represented by $R^6$ include those described above. Of those, a lower alkyl group is preferred. In the general formula (I), the alkyl group represented by $R^6$ is, for example, preferably a linear or branched alkyl group having 1 to 6 carbon atoms, more preferably a linear or branched alkyl group having 1 to 3 carbon atoms, particularly preferably a methyl group.

In the general formula (I), $R^7$ represents a hydrogen atom, a halogen atom, or an alkyl group. In the general formula (I), $R^7$ preferably represents, for example, a hydrogen atom or a halogen atom. Of those, a halogen atom is more preferred.

In the general formula (I), examples of the halogen atom represented by $R^7$ include fluorine, chlorine, bromine, and iodine atoms. Of those, for example, chlorine and bromine atoms are preferred.

In the general formula (I), examples of the alkyl group represented by $R^7$ include those described above. Of those, a lower alkyl group is preferred. In the general formula (I), the alkyl group represented by $R^7$ is, for example, preferably a linear or branched alkyl group having 1 to 6 carbon atoms, more preferably a linear or branched alkyl group having 1 to 3 carbon atoms, particularly preferably a methyl group.

$R^6$ and $R^7$ may form an unsaturated hydrocarbon six-membered ring together with a carbon atom to which $R^6$ is bonded and a carbon atom to which $R^7$ is bonded. The unsaturated hydrocarbon six-membered ring is, for example, a benzene ring. When $R^6$ and $R^7$ form a benzene ring together with a carbon atom to which $R^6$ is bonded and a carbon atom to which $R^7$ is bonded, the group:

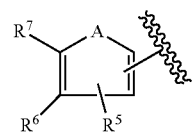

where —A—, $R^5$, $R^6$, and $R^7$ are as describe above, is the group:

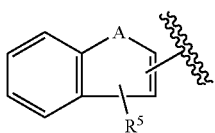

where —A— and $R^5$ are as described above.

In addition, in the present invention, in the general formula (I), the group:

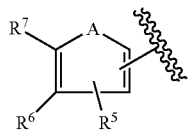

where —A—, $R^5$, $R^6$, and $R^7$ are as described above, means the group:

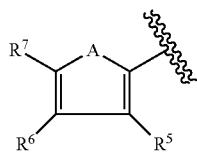

where —A—, $R^5$, $R^6$, and $R^7$ are as described above, or the group:

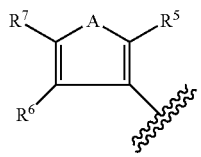

where —A—, $R^5$, $R^6$, and $R^7$ are as described above.

In the present invention, the group:

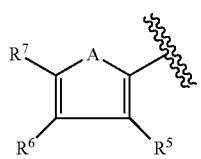

where —A—, $R^5$, $R^6$, and $R^7$ are as described above, is preferred.

In the present invention, preferred is a compound in which in the general formula (I),
—A— represents —NH—,
$R^1$, $R^4$, and $R^5$ all represent hydrogen atoms,
$R^2$ represents a hydrogen atom or an alkyl group,
$R^3$ represents a halogen atom or an alkyl group, and
$R^6$ and $R^7$ each represent a hydrogen atom or a halogen atom, and at least one of $R^6$ or $R^7$ represents a halogen atom.

Specifically, examples of the compound (I) include the following:

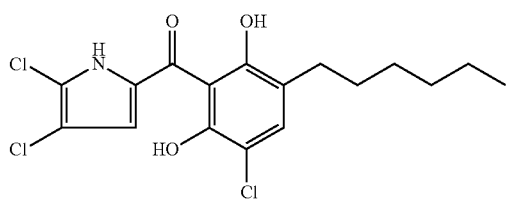

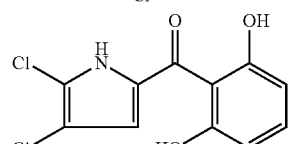

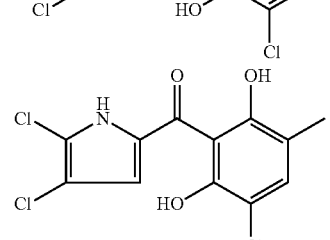

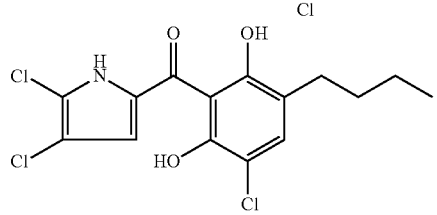

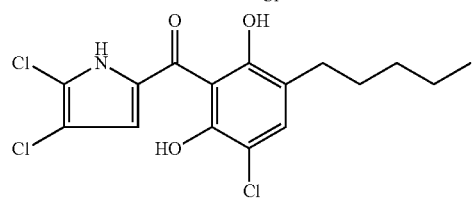

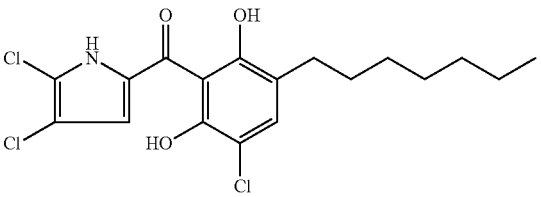

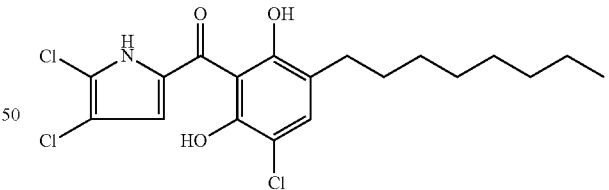

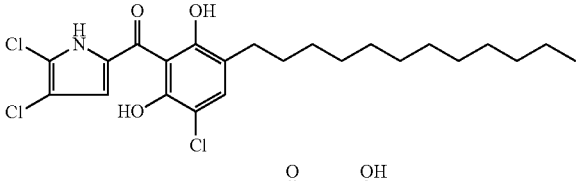

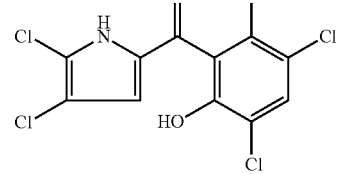

-continued

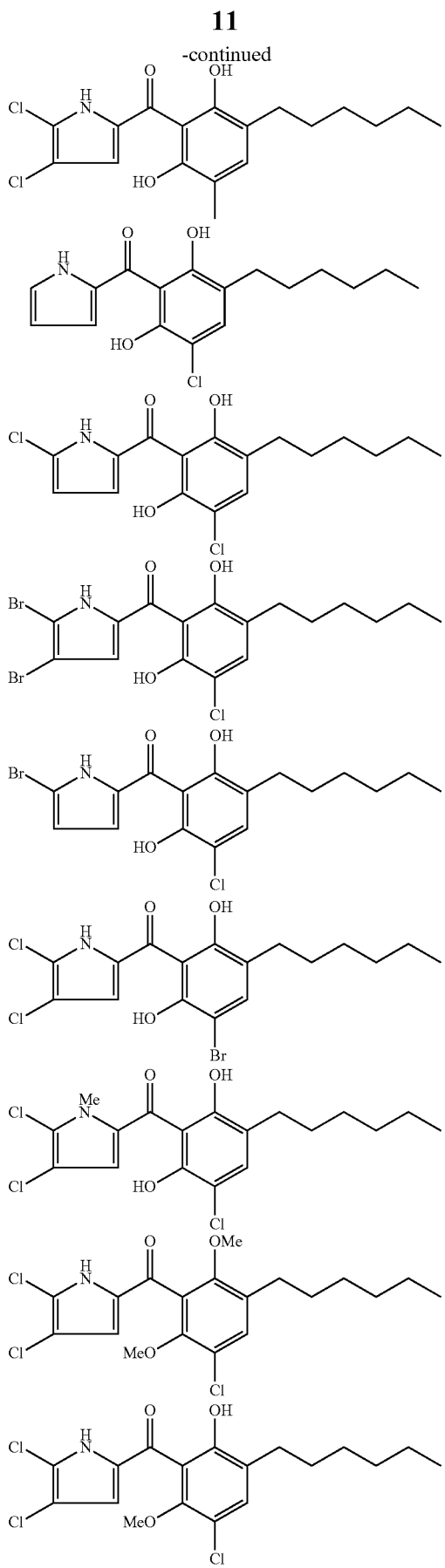
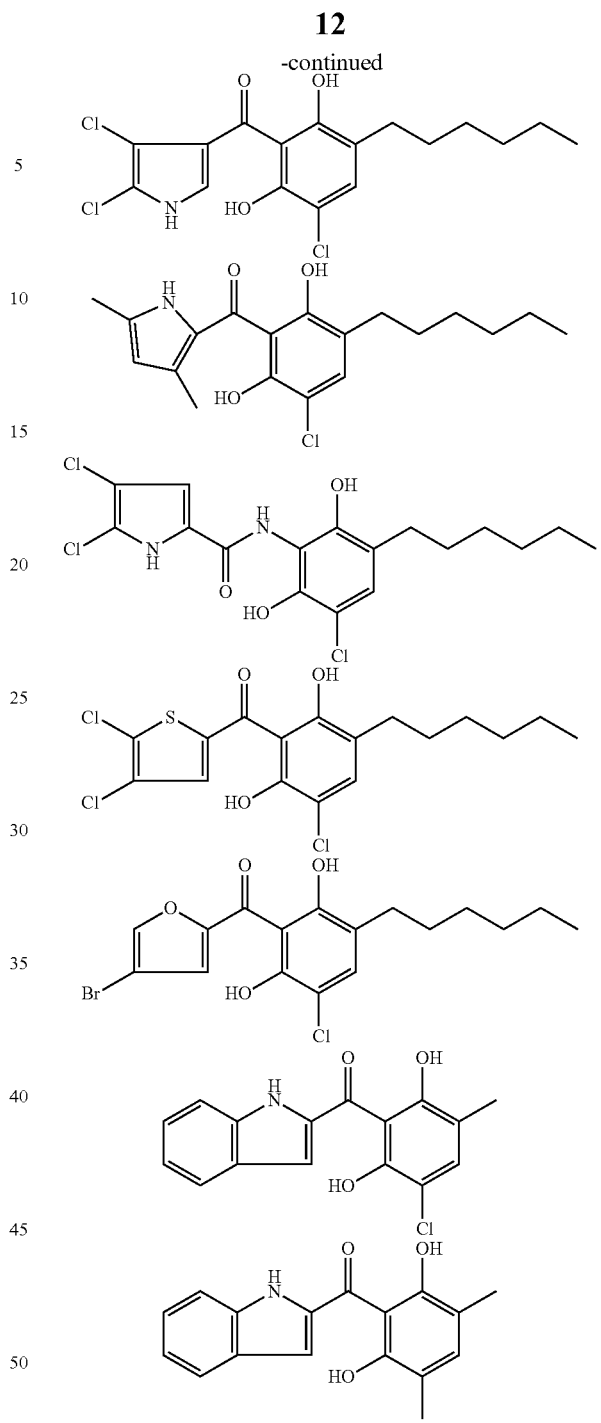

where MeO— represents a methoxy group.

The salt of the compound (I) serving as the active ingredient of the present invention encompasses an acid addition salt and a salt with a base. Specific examples of the acid addition salt include: inorganic acid salts, such as a hydrochloride, a hydrobromide, a hydroiodide, a sulfate, a perchlorate, and a phosphate; organic acid salts, such as an oxalate, a malonate, a succinate, a maleate, a fumarate, a lactate, a malate, a citrate, a tartrate, a benzoate, a trifluoroacetate, an acetate, a methanesulfonate, a p-toluenesulfonate, and a trifluoromethanesulfonate; and acidic amino acid salts, such as a glutamate and an aspartate. Specific examples of the salt with a base include: alkali metal or alkaline earth metal salts, such as a sodium salt, a potassium salt, and a calcium salt; salts with organic bases, such as a pyridine salt and a triethylamine salt; and salts with basic amino acids, such as lysine and arginine.

The compound (I) and the salt thereof serving as the active ingredient of the present invention may be present in the form of a hydrate or a solvate, and hence the compound serving as the active ingredient of the present invention also encompasses such hydrate and solvate.

A solvent forming the solvate is exemplified by alcohols, such as ethanol and propanol, organic acids, such as acetic acid, esters, such as ethyl acetate, ethers, such as tetrahydrofuran and diethyl ether, ketones, such as acetone, and dimethyl sulfoxide (DMSO).

In the present invention, the compound (I) or the salt thereof serving as the active ingredient of the present invention may be used alone as a preventive or therapeutic agent for pulmonary hypertension, or may be used as a pharmaceutical composition in combination with any of various pharmaceutically acceptable carriers (e.g., a tonicity agent, a chelating agent, a stabilizing agent, a pH regulator, a preservative, an antioxidant, a solubilizing agent, or a thickening agent).

Examples of the tonicity agent include: sugars, such as glucose trehalose, lactose, fructose, mannitol, xylitol, and sorbitol; polyhydric alcohols, such as glycerol, polyethylene glycol, and propylene glycol; and inorganic salts, such as sodium chloride, potassium chloride, and calcium chloride.

Examples of the chelating agent include: edentates, such as disodium edetate, calcium disodium edetate, trisodium edetate, tetrasodium edetate, and calcium edetate; ethylenediaminetetraacetate; nitrilotriacetic acid or salts thereof; sodium hexametaphosphate; and citric acid.

An example of the stabilizing agent is sodium hydrogen sulfite.

Examples of the pH regulator include acids, such as hydrochloric acid, carbonic acid, acetic acid, and citric acid, and also include: alkali metal hydroxides, such as sodium hydroxide and potassium hydroxide; alkali metal carbonates or hydrogen carbonates, such as sodium carbonate; alkali metal acetates, such as sodium acetate; alkali metal citrates, such as sodium citrate; and bases, such as trometamol.

Examples of the preservative include: sorbic acid; potassium sorbate; parahydroxybenzoate, such as methyl parahydroxybenzoate, ethyl parahydroxybenzoate, propyl parahydroxybenzoate, and butyl parahydroxybenzoate; quaternary ammonium salts, such as chlorhexidine gluconate, benzalkonium chloride, benzethonium chloride, and cetylpyridinium chloride; alkylpolyaminoethylglycine; chlorobutanol; polyquad; polyhexamethylene biguanide; chlorhexidine.

Examples of the antioxidant include sodium hydrogen sulfite, dried sodium sulfite, sodium pyrosulfite, and concentrated mixed tocopherols.

Examples of the solubilizing agent include sodium benzoate, glycerin, D-sorbitol, glucose, propylene glycol, hydroxypropyl methylcellulose, polyvinylpyrrolidone, macrogol, and D-mannitol.

Examples of the thickening agent include polyethylene glycol, methyl cellulose, ethyl cellulose, carmellose sodium, xanthan gum, sodium chondroitin sulfate, hydroxyethyl cellulose, hydroxypropyl cellulose, hydroxypropyl methylcellulose, polyvinylpyrrolidone, and polyvinyl alcohol.

In addition, the pharmaceutical composition may further contain, in addition to the compound (I) or the salt thereof, a compound known to have a preventive or therapeutic action on pulmonary hypertension. Examples of the compound known to have a preventive or therapeutic action on pulmonary hypertension include a prostacyclin preparation (e.g., epoprostenol), a PDE5 inhibitor (e.g., tadalafil), and an endothelin receptor antagonist (e.g., bosentan).

In the embodiment of the pharmaceutical composition, the content of the compound (I) or the salt thereof in the composition is not particularly limited, and may be appropriately set within, for example, conditions such as 90 mass % or more, 70 mass % or more, 50 mass % or more, 30 mass % or 10 mass % or more, 5 mass % or more, and 1 mass % or more in terms of the content of the compound (I).

A dosage form is not particularly limited, and examples thereof may include various dosage forms including: orally administered agents, such as a tablet, a pill, a capsule, a powder, a granule, and a syrup; and parenterally administered agents, such as an injection (e.g., intravenous injection, intramuscular injection, or local injection), a gargle, a drop, external preparations (an ointment, a cream, a patch, and an inhalant), and a suppository. Of the dosage forms, for example, orally administered agents (e.g., a tablet a pill, a capsule, a powder, a granule, and a syrup) and external preparations (e.g., an inhalant, an ointment, a cream, and a patch) are preferred.

In the present invention, the dose of the compound (I) or the salt thereof varies depending on, for example, an administration route and the age, body weight, or symptom of a patient, and hence cannot be uniquely defined. However, the dose only needs to be such an amount that a daily dose for adults is generally about 5,000 mg or less, preferably about 1,000 mg or less in terms of the dose of the compound (I). In addition, according to the present invention, the compound (I) exhibits an effect even at a low dose, and hence the dose may be, for example, such an amount that a daily dose for adults is about 100 mg or less, about 10 mg or less, about 8 mg or less, or about 5 mg or less in terms of the dose of the compound (I). The lower limit of the dose of the compound (I) or the salt thereof is also not particularly limited, and may be appropriately set within, for example, such a range that a daily dose for adults is generally 0.1 mg or more, preferably 0.5 mg or more in terms of the dose of the compound (I). When administered once daily, the compound (I) or the salt thereof only needs to be contained in the above-mentioned amount in a single dose. When administered three times daily, the compound (I) or the salt thereof only needs to be contained in an amount corresponding to one-third of the above-mentioned amount in a single dose.

The preventive or therapeutic agent for pulmonary hypertension of the present invention is administered to patients, such as mammals. Examples of the mammals include humans, monkeys, mice, rats, rabbits, cats, dogs, pigs, cattle, horses, and sheep. Of those, humans are preferred.

The preventive or therapeutic agent for pulmonary hypertension of the present invention prevents or treats and ameliorates pulmonary hypertension, in particular, idiopathic pulmonary arterial hypertension by at least suppressing excessive proliferation of pulmonary artery smooth muscle cells. Accordingly, the present invention also provides a suppressor for excessive proliferation of pulmonary artery smooth muscle cells containing a compound (I) or a salt thereof. It is known that out of the compounds (I) each serving as an active ingredient of the present invention, celastramycin (compound CEL-1 to be described later) binds to a zinc finger protein ZFC3H1 to inhibit signal transduction in which a transcription factor NF-κB is involved (Non-patent Literature 2). In addition, there is a previous report that a specific compound IMD-0354 (N-[3, 5-bis(trifluoromethyl)phenyl]-5-chloro-2-hydroxybenzamide) has an NF-κB-inhibiting action, suppresses the proliferation of pulmonary artery smooth muscle cells, and may have a therapeutic effect on pulmonary hypertension (Non-patent Literature 3). However, the compound (I) serving as the active ingredient of the present invention is a compound quite different in structure from IMD-0354 described above. Further, the inventors of the present invention examined N-p-tosyl-L-phenylalanine chloromethyl ketone, caffeic acid phenethyl ester, and Nα-p-tosyl-L-lysine chloromethyl ketone hydrochloride serving as compounds known to have NF-κB-inhibiting actions for their suppressive effects on the proliferation of pulmonary artery smooth muscle cells derived from patients with pulmonary hypertension by the same method as that described in Example 1 to be described later except that each of these compounds was added so that its final concentration was 5 μM. As a result, the proliferation of the pulmonary artery smooth muscle cells was not sufficiently suppressed (data not shown). Also from such viewpoints, the suppressive effect of the compound (I) on excessive proliferation of pulmonary artery smooth muscle cells and the preventive or therapeutic effect of the compound (I) on pulmonary hypertension in the present invention are unpredictable from the related art. The active ingredient, dosage form, dose, and the like of the suppressor for excessive proliferation of pulmonary artery smooth muscle cells are the same as those of the preventive or therapeutic agent for pulmonary hypertension.

The present invention is more specifically described below by way of Examples. However, the present invention is not limited thereto.

EXAMPLES

Example 1

The following compounds were used to assess the abilities of these compounds to suppress the proliferation of pulmonary artery smooth muscle cells from patients with pulmonary hypertension (IPAH-PASMC line: 1)

CEL-01

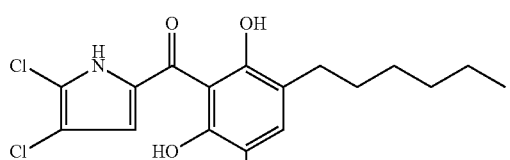

CEL-02

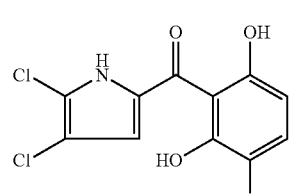

CEL-03

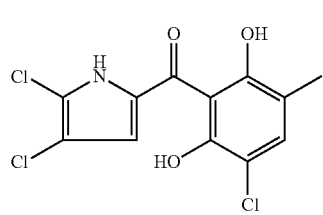

-continued

CEL-04

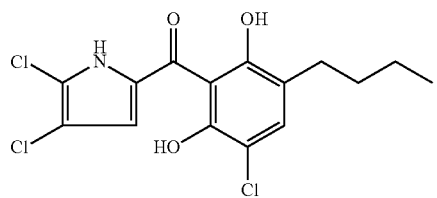

CEL-05

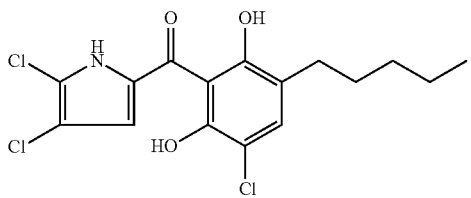

CEL-06

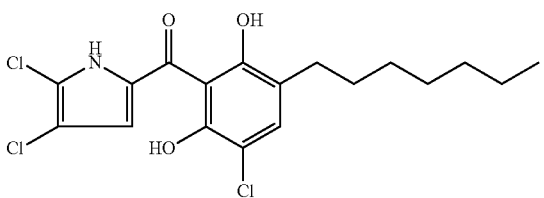

CEL-07

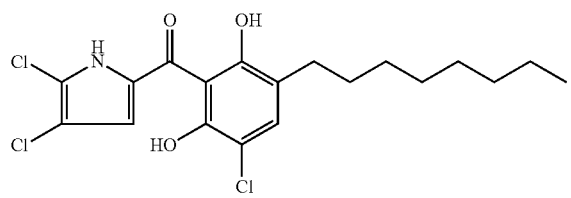

CEL-08

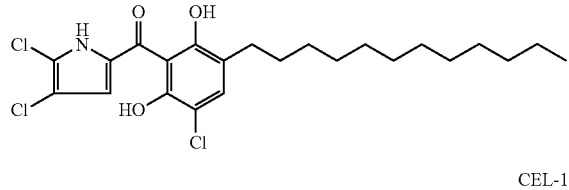

CEL-10

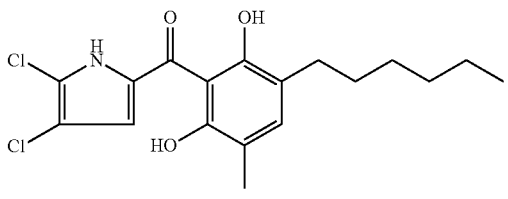

CEL-13

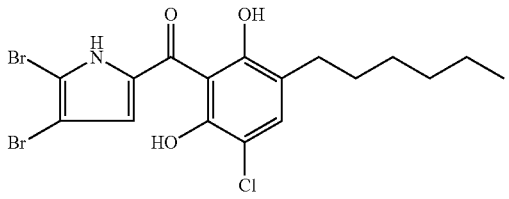

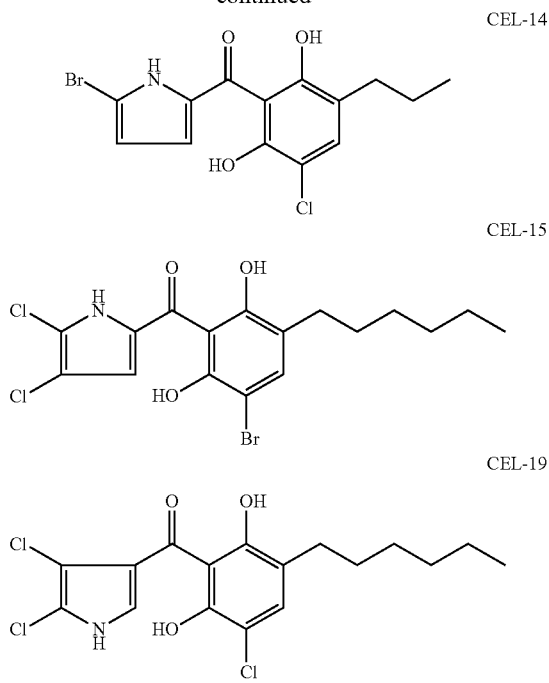

Those compounds were obtained by synthesis in the Faculty of Pharmaceutical Sciences, Tohoku University. Specifically, first, 66 μl each of pulmonary artery smooth muscle cells derived from patients with idiopathic pulmonary arterial hypertension (IPAH-PASMCs) suspended in a 10% FBS medium (DMEM supplemented with 10% FBS) were seeded in a 96-well plate at 50,000 cells/ml (day −1). 24 Hours after the cell seeding (the time point was defined as day 0), 33 μl each of 300 nM, 3 μM, and 15 μM solutions of CEL-1 to CEL-8, CEL-10, CEL-13 to CEL-15, and CEL-19 in 10% FBS containing 1% DMSO were added to the wells so that the final concentrations were 100 nM, 1 μM, and 5 μM, respectively. As a control, 33 μl of 10% FBS containing 1% DMSO was added in place of CEL-1 to CEL-8, CEL-10, CEL-13 to CEL-15, and CEL-19. On day 0 (immediately before the addition of each of CEL-1 to CEL-8, CEL-10, CEL-13 to CEL-15, and CEL-19), a cell viability was confirmed by performing CellTiter 96 (trademark) AQueous One Solution Cell Proliferation Assay, promega MTT assay. Further, 48 hours after the addition of each of CEL-1 to CEL-8, CEL-10, CEL-13 to CEL-15, and CEL-19 (day 2), the MTT assay was performed again to observe a change in cell viability. Thus, a cell proliferation-suppressing effect was assessed. The results are shown in Table 1 and FIG. 1.

TABLE 1

|  | 100 nM | 1 μM | 5 μM |
|---|---|---|---|
| 10% FBS | 1.40 | 1.40 | 1.40 |
| CEL-1 | 1.46 | 0.83 | 0.52 |
| CEL-2 | 1.37 | 1.36 | 0.87 |
| CEL-3 | 1.25 | 0.99 | 0.81 |
| CEL-4 | 1.24 | 0.79 | 0.53 |
| CEL-5 | 1.25 | 0.79 | 0.53 |
| CEL-6 | 1.23 | 0.77 | 0.54 |
| CEL-7 | 1.27 | 0.84 | 0.52 |
| CEL-8 | 1.13 | 0.74 | 0.47 |
| CEL-10 | 1.16 | 0.68 | 0.48 |
| CEL-13 | 1.20 | 0.72 | 0.51 |
| CEL-14 | 1.37 | 1.35 | 0.88 |
| CEL-15 | 1.26 | 0.78 | 0.54 |
| CEL-19 | 1.31 | 1.24 | 0.94 |

As shown in Table 1 and FIG. 1, it was found that a cell proliferation-suppressing effect on pulmonary artery smooth muscle cells derived from patients with idiopathic pulmonary arterial hypertension was obtained by the stimulation with each of CEL-1 to CEL-8, CEL-10, CEL-13 to CEL-15, and CEL-19 for 48 hours.

Figure 2:
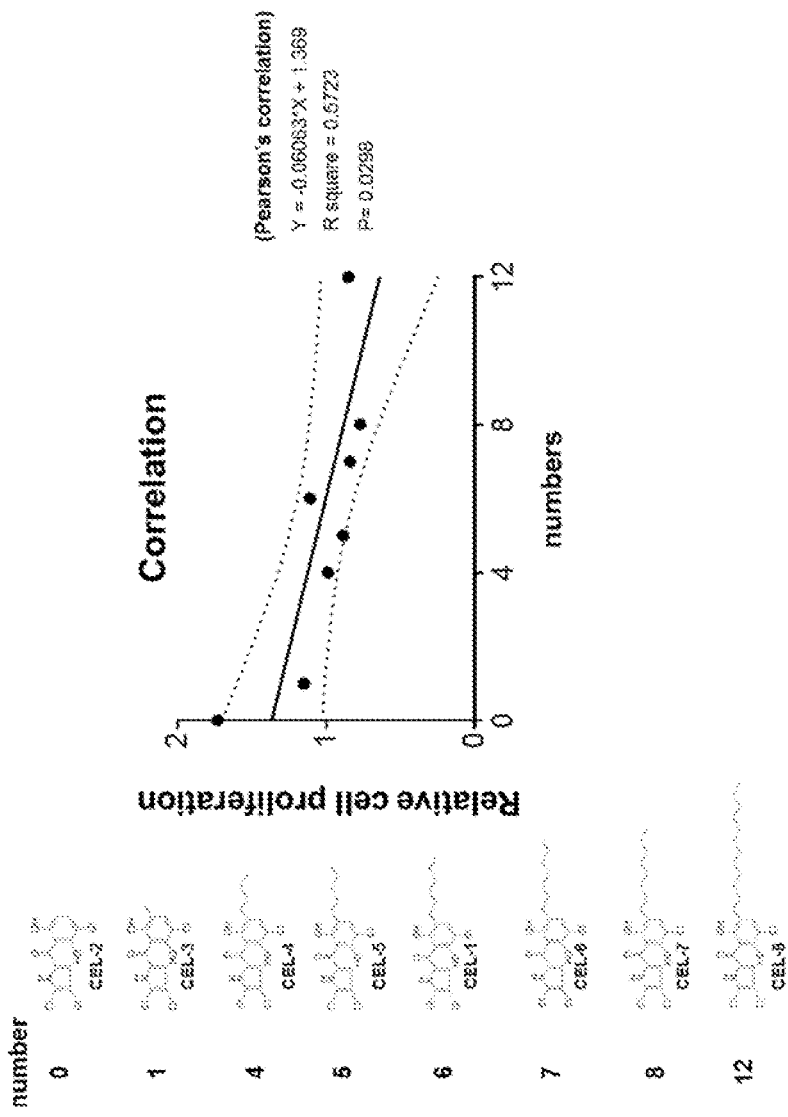
FIG. 2 is a graph for showing a relationship between the lengths of alkyl groups of compounds and day 2/day 0 cell number ratios in a test on an ability to suppress the proliferation of pulmonary artery smooth muscle cells from patients with pulmonary hypertension measured in Example 1.

In addition, in the case where $R^2$ in the general formula (I) represents an alkyl group, in order to explore an association between the length of the alkyl group and a pulmonary artery smooth muscle cell proliferation-suppressing effect, a test on an ability to suppress the proliferation of the pulmonary artery smooth muscle cells from patients with pulmonary hypertension (IPAH-PASMC line:1) was performed three times, and the lengths of alkyl groups of the respective compounds and the results of stimulation with the compounds at a concentration of 5 μM for 48 hours (averages of day 2/day 0 cell number ratios) were shown graphically. The graph is shown in FIG. 2. A Pearson's correlation test was performed on the lengths of the alkyl groups and the day 2/day 0 cell number ratios. As a result, a significant correlation was found with a P-value of 0.0298. Accordingly, in the case where $R^2$ in the general formula (I) represents an alkyl group, it was found that the compound having a larger number of carbon atoms in the alkyl group tended to have a higher ability to suppress the proliferation of pulmonary artery smooth muscle cells.

Example 2

Next, the therapeutic effect of CEL-3 on pulmonary hypertension was assessed in vivo. Specifically, the influence of CEL-3 on a hypoxia-induced pulmonary hypertension mouse model was investigated. The pulmonary hypertension mouse model was generated by breeding 9-week-old male C57BL/6 mice (n=14) in a hypoxic chamber having an oxygen concentration of from 8% to 12%. Before being housed in the hypoxic chamber, the mice were implanted with an osmotic pump containing CEL-3 dissolved with 50% DMSO, and were administered CEL-3 at 10 mg/kg/day by continuous subcutaneous infusion. The Vehicle group was administered a DMSO solution at the same concentration with an osmotic pump. The mice were bred in the hypoxic chamber for 3 weeks and then sacrificed to measure a right ventricular systolic pressure (RVSP) with a pressure catheter 1.2F (Transonic Scisense, US). In addition, after formalin fixation, the right ventricle and the left ventricle were separated to measure a right ventricle/(left ventricle plus septum) weight ratio RV/[LV+S]). Then, the extent of pulmonary hypertension was assessed on the basis of those results. The body weights of the Vehicle group and the CEL-3 administration group before the test were each 25.6±0.3 g. In addition, the body weights of the Vehicle group and the CEL-3 administration group after the test were 24.2±0.8 g and 23.9±0.7 g, respectively.

Figure 3:
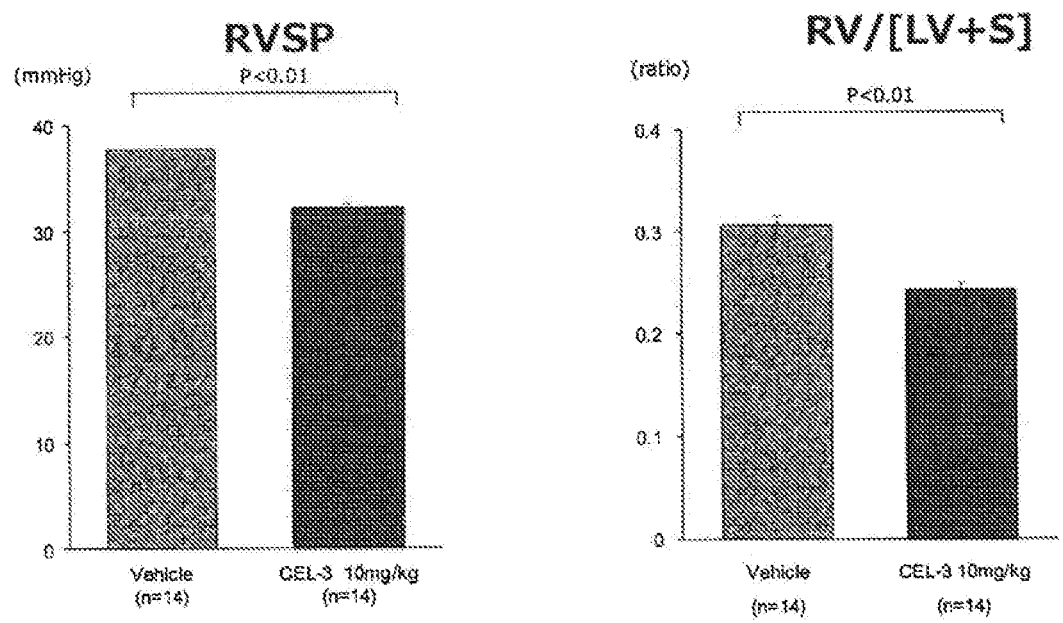
FIG. 3 are graphs for showing the influences of CEL-3 on RVSP and RV/[LV+S] in a pulmonary hypertension animal model measured in Example 2.

The results are shown in FIG. 3. As shown in FIG. 3, the results were that increases in right ventricular systolic pressure and right ventricle/(left ventricle plus septum) weight ratio were suppressed in the CEL-3 treatment group as compared to the control group, suggesting that the development of hypoxia-induced pulmonary hypertension was suppressed. That is, the results of the animal experiment were that the CEL-3 administration suppressed the increases in both of RVSP and RV/[LV+S] in the hypoxia-induced pulmonary hypertension mice, suggesting that CEL-3 had a preventive effect on pulmonary hypertension.

Example 3

Further, the influence of CEL-3 on an SU5416/hypoxia-induced pulmonary hypertension rat model, which served as a model exhibiting a pathological image most similar to that of human pulmonary arterial hypertension, was investigated. The pulmonary hypertension rat model was generated by: subcutaneously injecting 6-week-old male Sprague-Dawley rats (n=1.2) with SU5416 at 20 mg/kg; and then breeding the rats in a hypoxic chamber having an oxygen concentration of from 8% to 12% for 3 weeks followed by breeding the rats under normoxia for 2 weeks. After the hypoxic stimulation for 3 weeks, the rats were intraperitoneally injected with CEL-3 dissolved with 10% DMSO at 3 mg/kg daily for 2 weeks. The Vehicle group was intraperitoneally injected with a DMSO solution at the same concentration. The rats were treated with CEL-3 for 2 weeks and then sacrificed to measure a right ventricular systolic pressure (RVSP) with a pressure catheter 1.6F (Transonic Scisense, US). In addition, after formalin fixation, the right ventricle and the left ventricle were separated to measure a right ventricle/(left ventricle plus septum) weight ratio (RV/[LV+S]). Then, the extent of pulmonary hypertension was assessed on the basis of those results. The body weights of the Control group, the Vehicle group, and the CEL-3 administration group before the test were 160.8±1.7 g, 163.4±2.5 g, and 158.9±1.9 g, respectively. In addition, the body weights of the Control group, the Vehicle group, and the CEL-3 administration group after the test were 355.4±5.1 g, 264.91±9.3 g, and 260.0±11.1 g, respectively.

Figure 4:
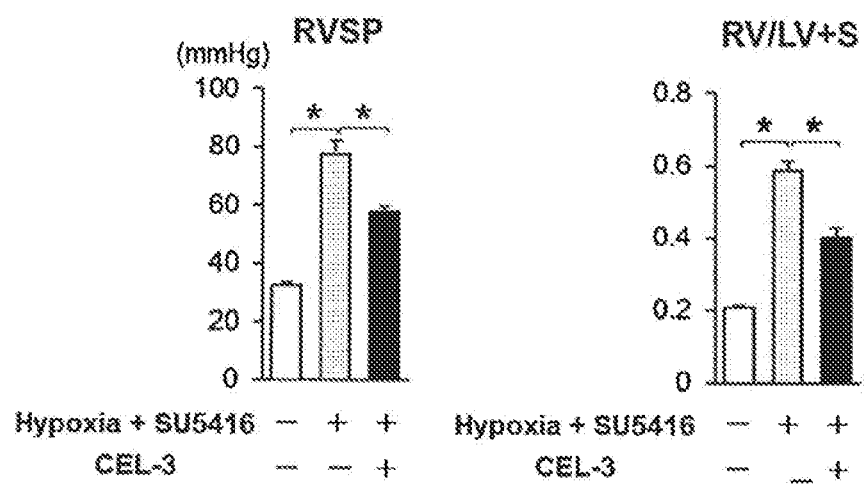
FIG. 4 are graphs for showing the influences of CEL-3 on RVSP and RV/[LV+S] in an SU5416/hypoxia-induced pulmonary hypertension rat model measured in Example 3.

The results are shown in FIG. 4. As shown in FIG. 4, the results were that increases in right ventricular systolic pressure and right ventricle/(left ventricle plus septum) weight ratio were suppressed in the CEL-3 treatment group as compared to the control group, suggesting that the development of SU5416/hypoxia-induced pulmonary hypertension was suppressed. That is, the results of the animal experiment were that the CEL-3 administration suppressed the increases in both of RVSP and RV/[LV+S] in the hypoxia-induced pulmonary hypertension rat, suggesting that CEL-3 had a preventive effect on pulmonary hypertension.

The invention claimed is:

1. A method of preventing or treating pulmonary hypertension, comprising administering an effective dose of a compound represented by the following formula (I) or a salt thereof to a patient in need of the prevention or treatment of pulmonary hypertension:

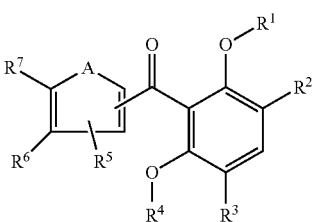

(I)

where: —A— represents —NH—, —S—, or —O—; $R^1$ and $R^2$ are identical to or different from each other, and each represent a hydrogen atom or an alkyl group; $R^3$ represents a hydrogen atom, a halogen atom, or an alkyl group; $R^4$ represents a hydrogen atom or an alkyl group; $R^5$ represents a hydrogen atom or an alkyl group; $R^6$ and $R^7$ are identical to or different from each other, and each represent a hydrogen atom, a halogen atom, or an alkyl group; and $R^6$ and $R^7$ may form an unsaturated hydrocarbon six-membered ring together with a carbon atom to which $R^6$ is bonded and a carbon atom to which $R^7$ is bonded.

2. The method according to claim 1, wherein —A— represents —NH—.

3. The method according to claim 1, wherein $R^1$ and $R^4$ both represent hydrogen atoms.

4. The method according to claim 1, wherein $R^5$ represents a hydrogen atom.

5. The method according to claim 1, wherein $R^6$ and $R^7$ each represent a hydrogen atom or a halogen atom, and at least one thereof represents a halogen atom.

6. The method according to claim 1, wherein $R^3$ represents a halogen atom or an alkyl group.

7. The method according to claim 1, wherein $R^2$ represents a hydrogen atom or an alkyl group.

8. The method according to claim 1,
wherein —A— represents —NH—,
wherein $R^1$, $R^4$, and $R^5$ all represent hydrogen atoms,
wherein $R^2$ represents a hydrogen atom or an alkyl group,
wherein $R^3$ represents a halogen atom or an alkyl group, and
wherein $R^6$ and $R^7$ each represent a hydrogen atom or a halogen atom, and at least one thereof represents a halogen atom.

9. The method according to claim 1, wherein $R^2$ represents a linear alkyl group having 4 or more carbon atoms.

10. The method according to claim 1, wherein $R^2$ represents a linear alkyl group having 7 or more carbon atoms.

11. The method according to claim 1, wherein the patient has pulmonary hypertension.

12. A method of preventing or treating pulmonary hypertension, comprising orally administering an effective dose of a compound represented by the following formula (I) or a salt thereof:

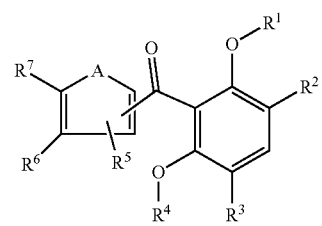

(I)

where: —A— represents —NH—, —S—, or —O—; $R^1$ and $R^2$ are identical to or different from each other, and each represent a hydrogen atom or an alkyl group; $R^3$ represents a hydrogen atom, a halogen atom, or an alkyl group; $R^4$ represents a hydrogen atom or an alkyl group; $R^5$ represents a hydrogen atom or an alkyl group; $R^6$ and $R^7$ are identical to or different from each other, and each represent a hydrogen atom, a halogen atom, or an alkyl group; and $R^6$ and $R^7$ may form an unsaturated hydrocarbon six-membered ring together with a carbon atom to which $R^6$ is bonded and a carbon atom to which $R^7$ is bonded.

\* \* \* \* \*